United States Patent [19]
Rasouli et al.

[11] Patent Number: 6,004,516
[45] Date of Patent: Dec. 21, 1999

[54] APPARATUS FOR GENERATING ODOR UPON ELECTRONIC SIGNAL DEMAND

[75] Inventors: Firooz Rasouli, Midlothian, Va.; Hamid Arastoopour, Downers Grove; Ali Oskouie, Chicago, both of Ill.

[73] Assignee: Illinois Institute of Technology, Chicago, Ill.

[21] Appl. No.: 08/907,230

[22] Filed: Aug. 6, 1997

Related U.S. Application Data

[60] Provisional application No. 60/023,465, Aug. 6, 1996.

[51] Int. Cl.⁶ ........................................ A61L 9/00
[52] U.S. Cl. .................... 422/124; 422/123; 422/125; 422/305; 422/306; 239/57; 239/60; 392/386; 392/390
[58] Field of Search ............................. 422/4, 5, 22, 120, 422/122, 123, 124, 125, 305, 306; 239/57, 60; 392/386, 390

[56] References Cited

U.S. PATENT DOCUMENTS

| | | |
|---|---|---|
| 2,562,959 | 8/1951 | Stern . |
| 2,871,526 | 2/1959 | Bulloff ...................................... 21/108 |
| 4,009,384 | 2/1977 | Holland . |
| 4,037,352 | 7/1977 | Hennart et al. ........................... 43/129 |
| 4,556,539 | 12/1985 | Spector ........................................ 422/5 |
| 4,603,030 | 7/1986 | McCarthy .................................... 422/4 |
| 4,604,114 | 8/1986 | Ward ......................................... 55/279 |
| 4,905,112 | 2/1990 | Rhodes .................................... 422/124 |
| 5,023,020 | 6/1991 | Machida et al. ......................... 422/124 |
| 5,069,876 | 12/1991 | Oshinsky ..................................... 422/4 |
| 5,069,877 | 12/1991 | Pozzo ......................................... 422/4 |
| 5,178,839 | 1/1993 | Spector .................................... 422/123 |
| 5,217,696 | 6/1993 | Wolverton et al. ..................... 422/121 |
| 5,273,690 | 12/1993 | McDowell .............................. 422/124 |
| 5,424,049 | 6/1995 | Giolitti et al. .......................... 422/305 |
| 5,565,148 | 10/1996 | Pendergrass ............................ 422/124 |
| 5,574,821 | 11/1996 | Babasade ................................ 392/392 |
| 5,591,409 | 1/1997 | Watkins ................................... 422/110 |
| 5,734,590 | 3/1998 | Tebbe .................................. 364/514 A |

FOREIGN PATENT DOCUMENTS

| | | |
|---|---|---|
| 0123746 | 7/1984 | European Pat. Off. . |
| 0238983 | 9/1987 | European Pat. Off. . |
| 2501468 | 9/1982 | France . |
| 2279010 | 12/1994 | United Kingdom . |

*Primary Examiner*—Robert J. Warden, Sr.
*Assistant Examiner*—Fariborz Moazzam
*Attorney, Agent, or Firm*—Pauley Petersen Kinne & Fejer

[57] ABSTRACT

An apparatus for generating odor upon electronic signal demand using a disk having an aroma-impregnated adsorbent and a substrate. The disk is inserted into a disk drive that receives signals from a user and/or a server computer. A controller within the disk drive supplies an electric, mechanical or thermal signal to the disk, resulting in the heating of the adsorbent. The controller may also activate a blower to distribute the scent produced by the heated adsorbent and to cool the adsorbent at the end of the scent distribution cycle.

21 Claims, 3 Drawing Sheets

APPARATUS FOR GENERATING ODOR UPON ELECTRONIC SIGNAL DEMAND

CROSS REFERENCE TO RELATED APPLICATION

This application claims the benefit of U.S. Provisional Application No. 60/023,465, filed Aug. 6, 1996, the disclosure of which earlier application is hereby incorporated by reference herein and made a part hereof, including but not limited to those portions which specifically appear hereinafter.

BACKGROUND OF THE INVENTION

1. Field of the Invention

This invention relates to an apparatus for generating odor in which a controller signal, possibly from a remote location, activates a heater that heats an aroma-impregnated adsorbent.

2. Description of the Prior Art

The Internet is a relatively new and quickly developing medium for information transfer and all forms of commerce. Internet access allows the user, through an ordinary telephone line, to view true multimedia clips, including text, pictures, audio and video. One current void on the Internet is the ability for a consumer to sample scents and aromas of food products, perfumes, flowers, wines and other products wherein the scent of the product is an important factor.

The prior art teaches several methods of distributing a specific scent on demand. The application of heat is a known method of diffusing perfumes or other odorants into the atmosphere. Pozzo, U.S. Pat. No. 5,069,877 teaches a method and apparatus wherein heat is applied, from a source such as a lightbulb, to a perfume-impregnated heat shrink material, thus diffusing the perfume into the air. Holland, U.S. Pat. No. 4,009,384, teaches a similar apparatus wherein heat, from a lightbulb, is applied to a porous, perfume-impregnated, temperature-resistant material.

Stern, U.S. Pat. No. 2,562,959 teaches a system wherein compressors pump various scents through air pipes depending on an electromechanical signal generated by a film. The various scents are stored in liquid form until selected for dispersal when they are vaporized and distributed through compressed air pipe lines.

There is a need, however, for an apparatus that permits a user to access any number of specific scents or fragrances, specifically through a signal provided from a remote location such as an Internet server.

SUMMARY OF THE INVENTION

It is one object of this invention to provide an apparatus which enables the user to sample various scents from a single disk.

It is another object of this invention to provide an apparatus that interfaces with a remote location and distribute selected scents based upon a predetermined signal.

It is still another object of this invention to provide an apparatus that interfaces with a personal computer to provide various scents based upon a predetermined signal.

It is yet another object of this invention to provide an apparatus that emits a selectable scent when an electric current is applied to the apparatus.

A user of the subject apparatus preferably operates a computer having a disk drive according to this invention, called a Tele-Aroma Drive (TAD). In one preferred embodiment of the subject invention, a user connects to a web site that is compatible with the subject apparatus and selects a specific scent from a computer menu. A controller, preferably contained within the disk drive generates an appropriate thermal or electrical signal to an exhaust and/or a disk containing an adsorbent. The adsorbent then disseminates the proper concentration of a scent into the user's environment.

The disk, preferably comprising a substrate and the adsorbent, is used as the means for delivery of the various scents or fragrances. In one preferred embodiment of this invention, a plurality of alternating strips of conductive material and non-conductive material are arranged on the substrate of a disk having a rectangular shape. In another preferred embodiment of the subject invention, a plurality of alternating concentric strips of conductive material and non-conductive material are arranged on the substrate of a circular disk. The adsorbent, such as a semi-porous polymer membrane, is preferably applied to the conductive material on the substrate.

A controller generates a signal, either thermal or electrical, to the disk and/or an exhaust. The controller preferably regulates the flow of electricity among power source, the disk and the exhaust. The controller preferably gathers signals from a user or a remote location such as a server, based upon predetermined characteristics of specific scent/adsorbent combinations.

A heater, such as a laser or a conductive element, heats the adsorbent depending on the specific signal received from the controller. The adsorbent, while heated, emits the specific scent from the disk. The exhaust passes a fluid, preferably air, over the adsorbent on the disk to distribute the scent emitted from the adsorbent into the environment.

The entire apparatus according to this invention is preferably housed within a disk drive, similar to a floppy disk drive used with personal computers. The disk drive can be connected to a computer with a dedicated card or through a printer port. In another preferred embodiment, a disk drive, similar to a CD-ROM drive used with personal computers, accommodates the disk formed from an arrangement of alternating concentric rings of conductive material and non-conductive material. In this preferred embodiment of this invention, the laser is used to generate heat within adsorbent.

BRIEF DESCRIPTION OF THE DRAWINGS

The above-mentioned and other features and objects of this invention will be better understood from the following detailed description taken in conjunction with the drawings wherein.

DESCRIPTION OF THE PREFERRED EMBODIMENTS

Figure 1:
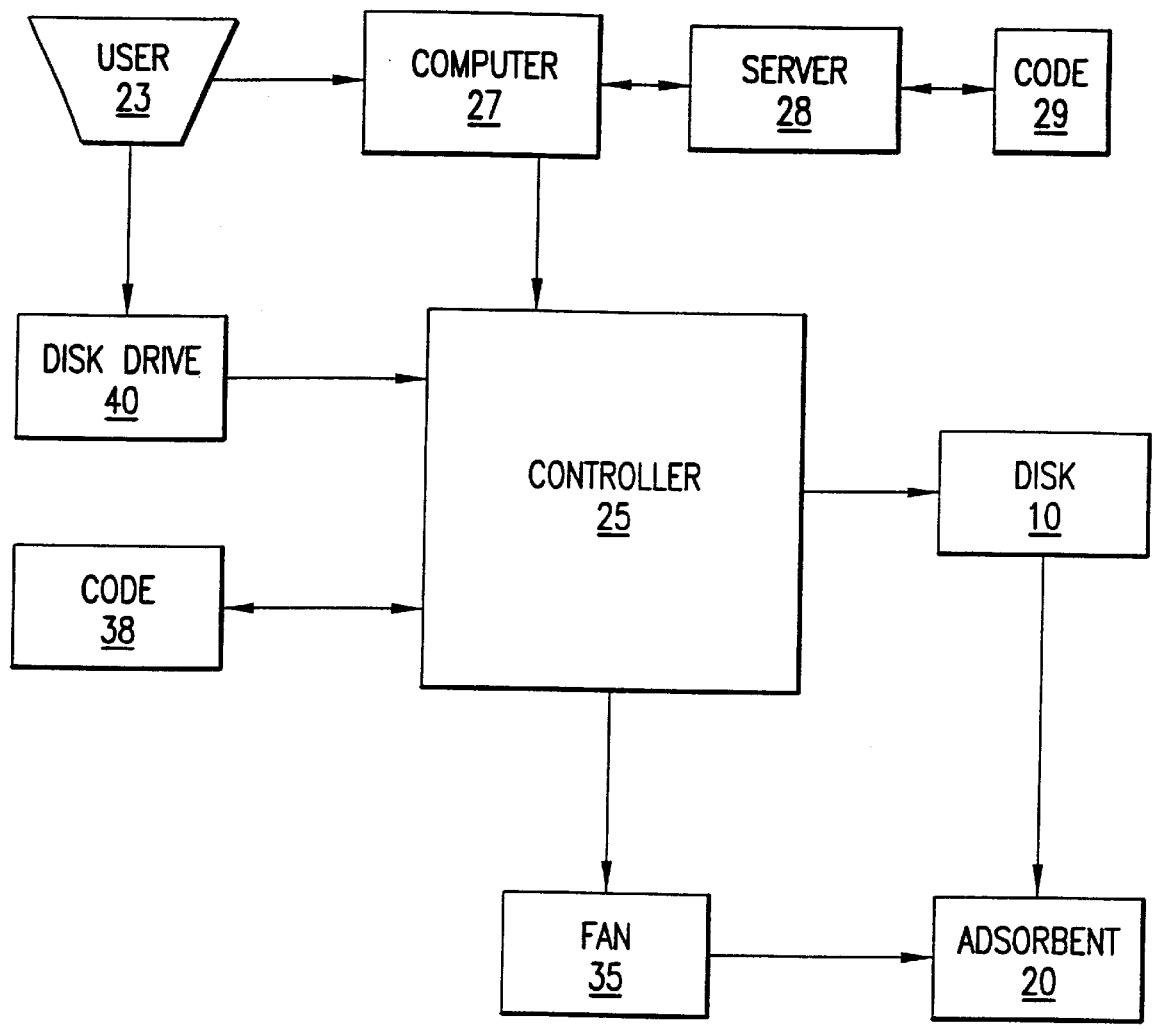
FIG. 1 is a flowchart of the interaction among the various components of the subject invention according to one preferred embodiment of this invention.

FIG. 1 shows a flowchart of the interaction among the various components of the apparatus according to one preferred embodiment of this invention. As shown in FIG. 1, user 23 of the subject apparatus preferably operates computer 27 with disk drive 40, also called a Tele-Aroma Drive or TAD.

In one preferred embodiment of the subject invention, user 23 connects from computer 27 to a web site on server 28 that is compatible with the subject apparatus. User 23 selects a specific scent from a menu, such as a perfume. Server 28 receives the signal from computer 27 and consults server code 29 for the proper signal to transmit back to computer 27. Server 28 transmits a return signal back to computer 27 based upon parameters of the selected perfume. This return signal is decoded by controller 25, which is preferably but not necessarily contained within disk drive 40. Controller 25 consults controller code 38 to generate the appropriate thermal or electrical power to fan 35 and/or disk 10 containing adsorbent 20. Given the proper power, adsorbent 20 disseminates the proper concentration of scent into an environment surrounding user 23.

Figure 2:
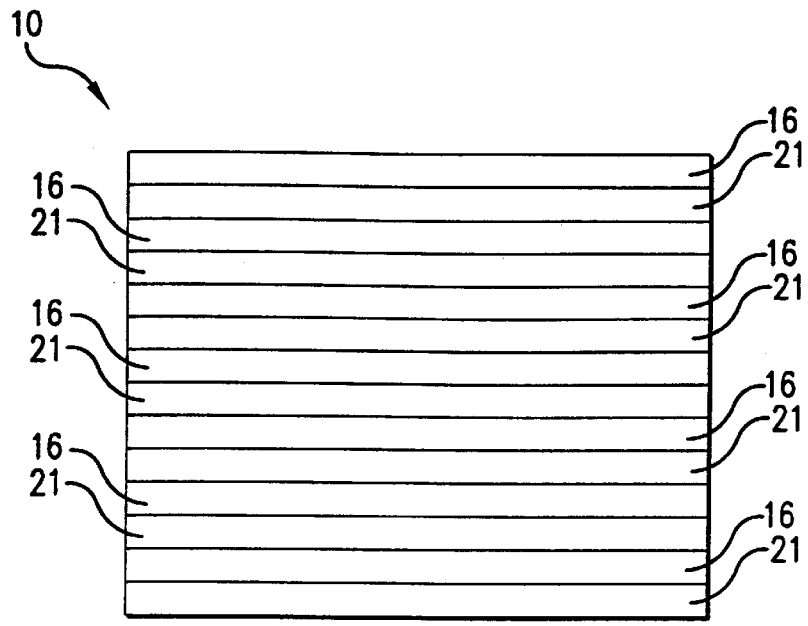
FIG. 2 is a diagrammatic top view of a disk according to one preferred embodiment of this invention.

An apparatus for generating odor utilizes disk 10 such as that shown in FIG. 2. Disk 10 preferably comprises two basic components: a substrate and adsorbent 20. Substrate, as used in this specification, is a generic term referring to the basic composition or support material of disk 10. Substrate material is preferably a polymer or other suitable non-conductive material.

Figure 4:
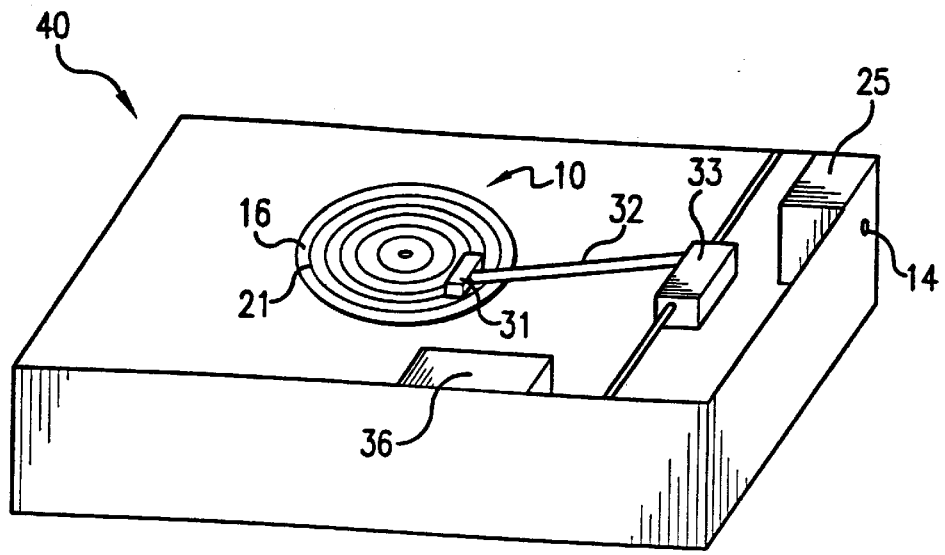
FIG. 4 is a diagrammatic perspective view of the apparatus according to another preferred embodiment of this invention.

In one preferred embodiment of this invention shown in FIG. 2, a plurality of alternating strips of conductive material 16 and non-conductive material 21 are arranged on the substrate of disk 10 having a rectangular shape. FIG. 4 shows another preferred embodiment of the subject invention in which a plurality of alternating concentric strips of conductive material 16 and non-conductive material 21 are arranged on the substrate of disk 10 having a circular shape.

Conductive material 16 may be a highly conductive metal such as aluminum or copper, or a conductive non-metal such as carbon. The strips or rings of conductive material 16 are preferably connected together with non-conductive material 21 to allow the strips of conductive material 16 to heat up or accept an electrical current independently of other strips of conductive material 16.

Adsorbent 20, as used in this specification, is a generic term referring to material that adsorbs desired odor-producing chemicals, such as aroma solutions and perfumes. The function of adsorbent 20 is to adsorb the odor-producing chemical when treated and desorb the odor-producing chemical when a stimulus, such as heat or high temperature air flow, is applied.

Adsorbent 20 is selected based upon several important criteria. Adsorbent 20 must have reasonable permeability. It is preferable that the characteristics of adsorbent 20 allow for the transport of aroma solution. Adsorbent 20 must also have a high capacity for the aroma solution. An ideal adsorbent 20 should retain a large amount of aroma solution per unit volume of adsorbent 20. Adsorbent 20 should also possess indiscriminate permeability to all ingredients of the aroma solution. An ideal adsorbent 20 will pass all components of the aroma solution evenly. Adsorbent 20 should also be inert such that no chemical interaction takes place between adsorbent 20 and the aroma solution. Adsorbent 20 should not desorb the aroma solution at temperatures under 100° F. Finally, adsorbent 20 should possess a resistance to high and variant temperatures, between 120° F. and 500° F., and cyclical heating and reheating such that adsorbent 20 characteristics do not change.

In one preferred embodiment of this invention, adsorbent 20 is applied to conductive material 16 on the substrate. Adsorbent 20 may be a gel, a paste or any other material that exhibits the characteristics described above. Other possible adsorbent 20 materials include: packing materials used in chromatography such as; Chromosorb 101™ packing material, Porpak Q™ packing material, Apiezon L™ packing material, Carbowax20 M™ packing material, OV-210™ packing material, and/or Dexsil 300 GC™ packing material; inorganic materials such as silica gel, activated carbon, carbon fiber, and/or zeolites; synthetic polymers and responsive polymeric materials that exhibit changes in properties in response to a control variable such as temperature or light; and/or organic compounds such as cellulose compounds, waxes or natural pastes made with mixtures of finely sifted sawdust and syrup of gum arabic.

In a preferred embodiment of this invention, adsorbent 20 is a semiporous membrane 22. Specifically, such materials as Teflon™ polytetrafluoroethylene, Tygon™ polymer, silicon rubber or other polymers may be used as adsorbent 20. Silicon rubber demonstrates favorable results according to the desired characteristics listed above for an ideal adsorbent 20. In the embodiment of this invention wherein adsorbent 20 is a polymer such as semi-porous membrane 22, adsorbent must be treated in one of several methods to suspend the aroma solution or fragrance within pores of adsorbent 20. In an alternate preferred embodiment of this invention, key chemical ingredients can be mobilized in adsorbent 20, and by selective precise heating of combinations of such key chemical ingredients, various odors can be generated in-situ.

As shown by the flow chart in FIG. 1, controller 25 generates a signal to an input of the apparatus. The signal is dependent upon specifications or characteristics entered by user 23 from personal computer 27 or by a vendor from server computer 28. Controller 25 preferably regulates the flow of electricity among power source (not shown in FIG. 1), disk 10 and exhaust 35. As discussed above, controller 25 also gathers signals from a user or a remote location such as server 28 shown in FIG. 1 and, based upon predetermined characteristics of specific aroma solutions and adsorbents 20, generates an input, either thermal, mechanical or electrical, to disk 10 and/or exhaust 35.

Figure 6:
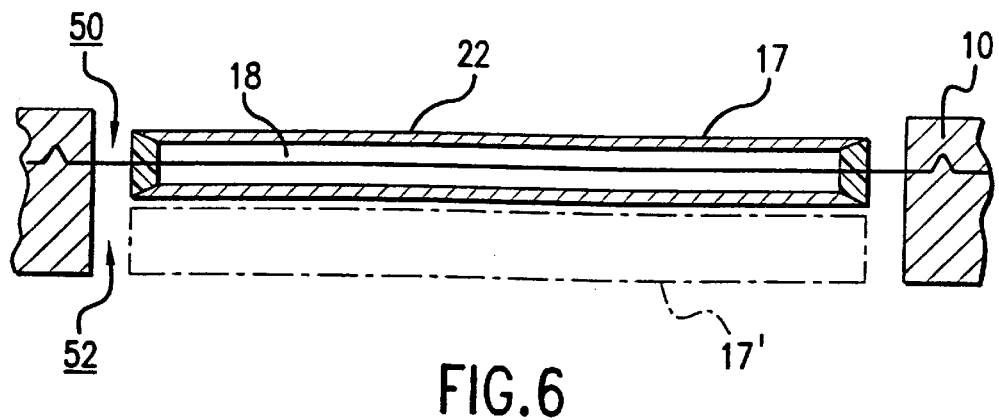
FIG. 6 is a diagrammatic cross-sectional side view of a membrane module according to one preferred embodiment of this invention.

Heater 30, such as laser 31 shown in FIG. 4 or conductive element 18 shown in FIG. 6, heats adsorbent 20 depending on the specific signal received from controller 25. Heater 30 reaches a predetermined temperature based upon a signal received from controller 25. The predetermined temperature is calculated based upon the chemical properties of the aroma solution to be distributed as well as the characteristics of the specific adsorbent 20. Each aroma solution/adsorbent 20 combination may require a slightly different temperature to effectively separate the scent from adsorbent 20. In one preferred embodiment of this invention, heater 30 is conductive element 18, such as that shown in FIG. 6 and discussed below. When a current is applied to conductive element 18, a desired temperature is attained with slight variations of the applied current.

In one preferred embodiment of this invention, a predetermined temperature is achieved by controlling the time of heating instead of the temperature of conductive element 18. Timed heating thus eliminates the need for a thermocouple connected to conductive element 18.

In another preferred embodiment of this invention, shown in FIG. 4, laser 31 is used to generate heat within adsorbent 20. If laser 31 is used as heater 30, an arrangement of alternating conductive material 16 and non-conductive material 21 is unnecessary. Like a CD-ROM disk, disk 10 in this preferred embodiment can be fabricated entirely from a non-conductive substrate, and adsorbent 20 can be arranged in concentric rings on such non-conductive substrate.

In yet another preferred embodiment of this invention, heater 30 may comprise a blower producing a high temperature, high temperature air flow. In this embodiment, high temperature gas, such as air, is discharged across the surface of adsorbent 20 to generate heat in adsorbent 20.

Adsorbent 20, while heated or exposed to a high-temperature, high-velocity gas, emits the specific aroma from disk 10. According to one preferred embodiment of this invention, exhaust 35, such as fan or blower 36, passes a fluid, preferably air, over adsorbent 20 on disk 10 and preferably through vents 45 in disk drive 40. In another preferred embodiment of this invention, exhaust 35 may discharge a high temperature air flow which initiates fast evaporation or sublimation of the aroma solution on adsorbent 20. Exhaust 35 preferably distributes the scent emitted from adsorbent 20 into the environment surrounding user 23, enhances adsorption of the scent, and cools heater 30 and adsorbent 20 to slow dissipation of further scent when a new scent is selected or the current scent is satisfactorily distributed. The combined distribution and cooling action of exhaust 35 avoids mixing multiple fragrances during extended use of the apparatus.

In another preferred embodiment of this invention, adsorbent 20 such as at least one membrane module 17 having semi-porous membrane 22, as shown in FIG. 6, is moveable from a first position to a second position within apparatus, such as disk 10. In this preferred embodiment, membrane module 17, when selected, moves from a first position in upper compartment 50 to a second position in lower compartment 52. Lower compartment 52 is preferably positioned within a discharge path of exhaust 35. This preferred embodiment of this invention prevents excess mixing of scents of the selected membrane module 17' with unselected membrane modules 17. Controller 25 preferably controls the movement of adsorbent 20 such as membrane module 17, 17' from a first position to a second position and vice versa.

The entire apparatus according to this invention is preferably housed within disk drive 40, much like a stagnant 3.5" floppy disk drive. Disk drive 40 is preferably not larger than a typical computer speaker, and may be purchased by a consumer like any other personal computer peripheral device. Disk drive 40 can be connected to computer 27 with a dedicated card or through a printer port to input 14 of disk drive 40. Disk 10 is preferably inserted into disk drive 40 which is configured with computer 27.

Figure 3:
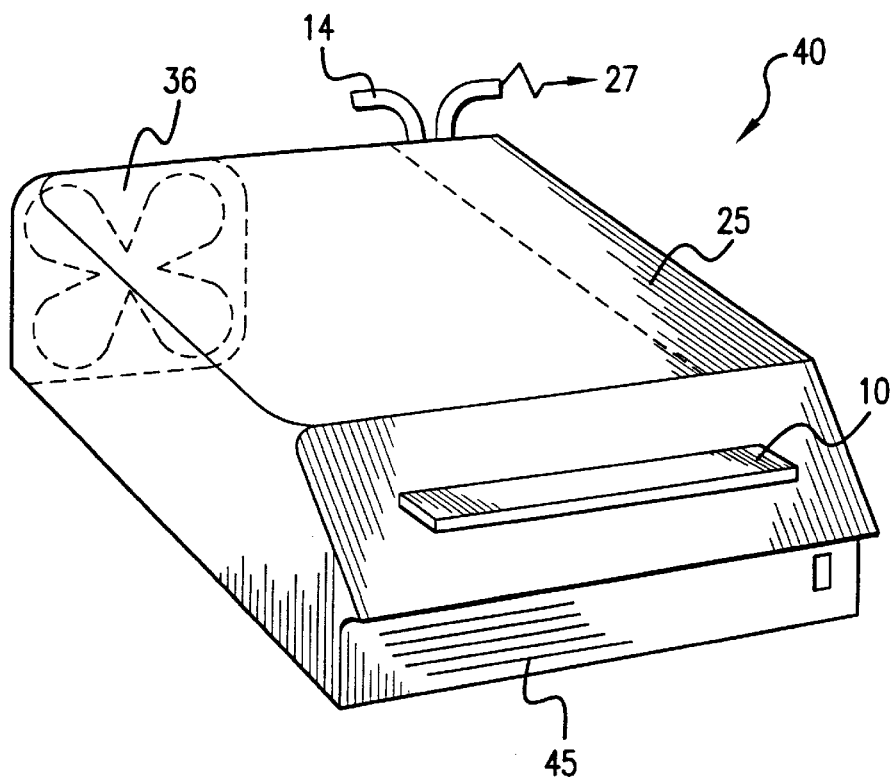
FIG. 3 is a diagrammatic perspective view of the apparatus according to one preferred embodiment of this invention.

In one preferred embodiment of this invention shown in FIG. 3, disk drive 40 accepts disk 10 such as that shown in FIG. 2. In disk drive 40 shown in FIG. 3, controller 25 applies various currents and/or thermal energy to strips of conductive material 16 or a matrix of conductive elements 18, such as those in membrane module 22 shown in FIG. 6.

Another preferred embodiment of this invention is shown in FIG. 4, wherein disk drive 40 having input 14 accommodates disk 10 formed from an arrangement of alternating concentric rings of conductive material 16 and non-conductive material 21. Disk drive 40 shown in FIG. 4 is configured similar to a CD-ROM drive used with personal computers. Disk drive 40 comprises actuator motor 33 which controls actuator arm 32 to position laser 31 at a predetermined radius of disk 10. A disk motor (not shown) rotates disk 10 so that laser 31 heats a specific concentric ring preferably layered with adsorbent 20.

Experimental Procedure

Figure 5:
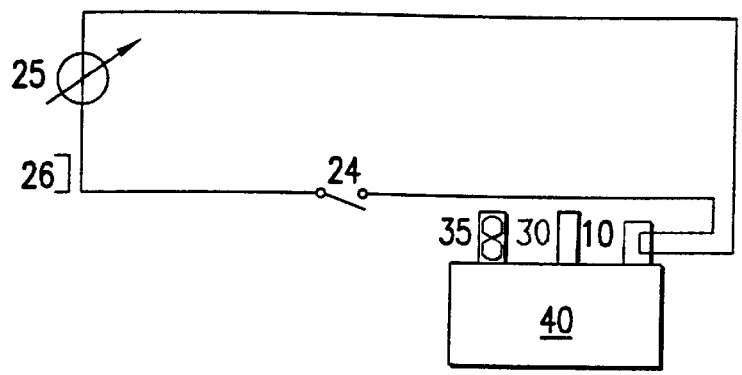
FIG. 5 is schematic view of the apparatus according to one preferred embodiment of this invention.

An experimental apparatus was developed to test different polymeric membranes for permeation of odor. A schematic of the experimental apparatus is shown in FIG. 5. In one preferred embodiment of the subject invention, controller 25 comprises a variable transformer (VARIAC) and switch 24 for distributing the appropriate currents to input 14 of disk drive 40.

In one preferred embodiment of this invention, disk 10 comprises six pairs of inputs electrically connected with six corresponding membrane modules 17 arranged in a row. Each membrane module 17 in this experimental embodiment comprises conductive element 18 surrounded with semi-porous membrane 22. For the purposes of this experiment, semi-porous membrane 22 is formed into a tube surrounding conductive element 18.

Several polymeric materials including Teflon™ polytetrafluoroethylene, Tygon™ polymer and silicon rubber were tested for use as semi-porous membrane 22. Silicon rubber was chosen for this experiment based upon its beneficial characteristics. The silicon rubber was formed into tubes, having an internal surface and an external surface, for use as semi-porous membrane 22 of membrane module 17. For this experiment, silicon rubber tubing approximately 2 inches in length were used as semi-porous membrane 22. Various thicknesses of semi-porous membrane 22 were investigated.

Appropriate aroma solutions, in this case various commercially available perfumes, were injected, each in a separate membrane module 17, between the annulus formed between conductive element 18 and semi-porous membrane 22. Aroma solution was drained from semi-porous membrane 22 after an appropriate soaking time, in this case approximately 48 hours. Alternatively, aroma solution may remain within semi-porous membrane 22. In another preferred embodiment, the external surface of semi-porous membrane 22 was soaked with aroma solution. In this experiment, each membrane module 17 was filled with 0.2 ml of perfume.

Each membrane module 22 was assembled using conductive element 18 made with 24 BNC Nickel-Chrome resistance wire. Conductive element 18 was fed through the center of semi-porous membrane 17 and each end of semi-porous membrane 22 was sealed using a fast-setting aluminum epoxy. For this experiment, a Teflon™ polytetrafluoroethylene sleeve was applied between conductive element 18 and semi-porous membrane 17 to prevent direct contact of the hot conductive element 18 with the semi-porous membrane 17.

Membrane modules 22 containing semi-porous membranes 17 treated with the aroma solution were then connected to power source 26. For experimental purposes, a 110 Volt power source 26 was transformed into approximately 3–4 Volts prior to application to membrane module 17.

Fan 35 with a flow rate of about 32 cfm (cubic feet per minute) was used as exhaust 35 to disseminate the fragrance of the aroma solution. In one preferred embodiment of this invention, air flow from fan 35 was directed over an exposed upper surface of membrane modules 17. In another, alternate embodiment air flow was directed beneath the surface of membrane modules 17 through slots or compartment 52, shown in FIG. 6, constructed under each membrane module 17.

In yet another embodiment of this invention, shown in FIG. 6, membrane module 17 is moveable from a first position within upper compartment 50 to a second position in lower compartment 52. In this preferred embodiment of the invention, selected membrane module 17' is positioned in the path of air flow from fan 35 (not shown in FIG. 6). Membrane module 17 is movable from a first position to a second position using standard mechanical means, such as gears or belts, known to those having ordinary skill in the art.

A K-type thermocouple measured the surface temperature of each conductive element 18. The resulting electric signal was then recorded using a Strawberry Tree™ data acquisition and control system on a personal computer. The temperature of conductive element 18 was then controlled by the same system. The optimum temperature of conductive element 18, that is, the highest temperature possible without altering the properties of the aroma solution or damaging membrane module 17 was obtained by trial and error.

Experimental Results

Two air flow paths were tested, over the upper, exposed surface of membrane modules 17 and beneath the surface of membrane modules 17. Experimental results revealed that air flow over the upper surface of membrane module 17 results in better dispersal of the scent generated by membrane module 17. Directing the air beneath the surface of membrane modules 17 results in scents from differently scented membrane modules 17 intermingling. Membrane module 17' positioned in the path of air flow from fan 35 greatly reduced the mixing of scents from the various unselected membrane modules 17.

Tests also revealed that, to avoid mixing different scents among membrane modules 17, a delay of at least 15 seconds is necessary between the deactivation of one membrane module 17 and the activation of a different membrane module 17. However, such a delay was unnecessary in the embodiment of this invention wherein membrane module 17' is moveable to a second position.

Test results revealed that the thickness of semi-porous membrane 22 was proportional to the time lag for detection of the scent of membrane module 17. Experimental results also revealed that soaking only the inner surface of the semi-porous membrane 22 results in better dissemination of the scent from membrane module 17. Membrane module 17 could be reused many times before requiring replacement and/or reapplication of aroma solution.

Because each perfume has different characteristics, the required temperature of conductive element 18 was different for each brand of perfume. This suggests that the selection of the temperature should be done automatically when the type of aroma solution, such as a brand of perfume, is specified.

While in the foregoing specification this invention has been described in relation to certain preferred embodiments thereof, and many details have been set forth for purposes of illustration, it will be apparent to those skilled in the art that the apparatus is susceptible to additional embodiments and that certain of the details described herein can be varied considerably without departing from the basic principles of the invention.

We claim:

1. A system for generating odor, the system comprising:
    an apparatus for containing a substrate;
    a plurality of adsorbents deposited in a fixed position on the substrate, each adsorbent retaining a releasable aroma, wherein a plurality of alternating strips of a conductive material and a non-conductive material are arranged on the substrate;
    a controller separate from the apparatus generating a signal on demand from the controller, an input of the apparatus accepting the signal;
    a heater simultaneously heating one or more adsorbents of the plurality of adsorbents upon demand as a function of the signal; and
    an exhaust discharging a fluid over the one or more adsorbents.

2. The apparatus of claim 1 wherein the at least one adsorbent is deposited on the conductive material.

3. The apparatus of claim 1 wherein the at least one adsorbent is a polymer membrane.

4. The apparatus of claim 1 wherein the at least one adsorbent is movable from a first position to a second position.

5. The apparatus of claim 1 wherein the heater comprises a conductive element in communication with an electric current supply.

6. The apparatus of claim 1 wherein the heater comprises a laser.

7. The apparatus of claim 1 wherein the controller comprises a computer.

8. The apparatus of claim 1 wherein the exhaust comprises a blower.

9. The apparatus of claim 1 wherein the exhaust discharges fluid over the at least one adsorbent as a function of the signal.

10. A system for generating odor, the system comprising:
    an apparatus for containing a substrate;
    a plurality of adsorbents deposited in a fixed position on the substrate, each adsorbent retaining a releasable aroma, wherein a plurality of alternating concentric rings of a conductive material and a non-conductive material are arranged on the substrate;
    a controller separate from the apparatus generating a signal on demand from the controller, an input of the apparatus accepting the signal;
    a heater simultaneously heating one or more adsorbents of the plurality or adsorbents upon demand as a function of the signal; and
    an exhaust discharging a fluid over the one or more adsorbents.

11. The apparatus of claim 10 wherein the at least one adsorbent is deposited on the conductive material.

12. An apparatus for generating odor, the apparatus comprising:
    a disk drive having an input;
    an aroma disk insertable within the disk drive comprising a plurality of membrane modules in communication with the input of the disk drive, a semi-porous membrane of each membrane module surrounding a conductive element, each membrane module retaining a releasable aroma;
    a controller generating a signal, the input of the disk drive accepting the signal;
    a heater simultaneously heating said one or more conductive elements upon demand as a function of the signal to the input of the disk drive; and
    an exhaust discharging a fluid over said one or more conductive elements.

13. The apparatus of claim 12 wherein the disk is encased in a protective enclosure.

14. The apparatus of claim 12 wherein the at least one membrane module is moveable from a first position to a second position.

15. The apparatus of claim 12 wherein the conductive element comprises a Nickel-Chrome resistance wire.

16. The apparatus of claim 12 wherein the semi-porous membrane is tubular.

17. The apparatus of claim 12 wherein the semi-porous membrane has a generally square cross-section.

18. The apparatus of claim 12 wherein at least one end of the tubular semi-porous membrane is sealed with epoxy.

19. The apparatus of claim 12 wherein the semi-porous membrane is impregnated with an aroma solution.

20. The apparatus of claim 12 wherein the exhaust discharges fluid over the conductive element as a function of the signal.

21. The apparatus of claim 12 further comprising a power source in electrical communication with the conductive element.

* * * * *